(12) United States Patent
Sasaki et al.

(10) Patent No.: US 11,576,710 B2
(45) Date of Patent: *Feb. 14, 2023

(54) DISPENSING SYSTEM AND METHOD

(71) Applicant: Medtronic Holding Company Sàrl, Neuchâtel (CH)

(72) Inventors: Neil Sasaki, San Jose, CA (US); Amy L. Arthur, San Jose, CA (US); Samuel V. Bolosan, San Jose, CA (US); Carl M. Kling, San Ramon, CA (US)

(73) Assignee: MEDTRONIC HOLDING COMPANY SARL, Tolochenaz (CH)

( * ) Notice: Subject to any disclaimer, the term of this patent is extended or adjusted under 35 U.S.C. 154(b) by 650 days.

This patent is subject to a terminal disclaimer.

(21) Appl. No.: 16/707,332

(22) Filed: Dec. 9, 2019

(65) Prior Publication Data

US 2020/0113612 A1 Apr. 16, 2020

Related U.S. Application Data

(62) Division of application No. 15/612,010, filed on Jun. 2, 2017, now Pat. No. 10,537,374.

(Continued)

(51) Int. Cl.
*A61B 17/88* (2006.01)
*B65D 81/32* (2006.01)
(Continued)

(52) U.S. Cl.
CPC ...... *A61B 17/8833* (2013.01); *A61B 17/8816* (2013.01); *A61B 17/8822* (2013.01);
(Continued)

(58) Field of Classification Search
CPC ............ A61B 17/8825; A61B 17/8833; A61B 17/8816; A61B 7/8822; A61F 2/4601
See application file for complete search history.

(56) References Cited

U.S. PATENT DOCUMENTS 10,357,300 B2 * 7/2019 Sasaki .................. B65D 81/325
2005/0113843 A1 5/2005 Arramon
(Continued)

FOREIGN PATENT DOCUMENTS

CN 102740779 A 10/2012
CN 105338915 B 2/2016
(Continued)

OTHER PUBLICATIONS

CNIRA—China—First Office Action—Application No. 201780032587. 6, Applicant: Medtronic Holding Company Sàrl, dated Nov. 25, 2020.
International Search Report and Written Opinion of the International Searching Authority, European Patent Office, PCT/IB2017/000767, dated Dec. 13, 2018.
PCT/IB2017/000767—International Search Report, Written Opinion of the International Searching Authority EPO, dated Nov. 23, 2017.

*Primary Examiner* — David W Bates
(74) *Attorney, Agent, or Firm* — Sorell, Leona & Schmidt, LLP (57) ABSTRACT

A dispensing system includes a device having a body extending along a longitudinal axis between opposite proximal and distal ends. The body includes a proximal chamber, a distal chamber and a wall between the chambers. The body includes a first port in communication with the proximal chamber and a second port in communication with the distal chamber. A shaft is movably positioned within the body. The shaft extending through the wall and comprising a proximal plunger positioned within the proximal chamber and a distal plunger positioned within the distal chamber. Wherein pressure introduced through an opening in the proximal end moves the shaft such that the proximal plunger moves a material within the proximal chamber out of the first port and the distal plunger moves a material within the distal chamber out of the second port. Kits and methods of use are disclosed.

20 Claims, 10 Drawing Sheets

Related U.S. Application Data (60) Provisional application No. 62/345,398, filed on Jun. 3, 2016.

(51) Int. Cl.

| | | |
|---|---|---|
| *B01F 25/4314* | (2022.01) | |
| *B01F 35/71* | (2022.01) | |
| *A61F 2/44* | (2006.01) | |
| *A61F 2/46* | (2006.01) | |
| *A61M 5/31* | (2006.01) | |

(52) U.S. Cl.
CPC .... *A61B 17/8825* (2013.01); *B01F 25/43141* (2022.01); *B01F 35/7174* (2022.01); *B65D 81/325* (2013.01); *A61B 17/8819* (2013.01); *A61B 2017/8838* (2013.01); *A61F 2/44* (2013.01); *A61F 2/4601* (2013.01); *A61M 5/31* (2013.01)

(56) References Cited

U.S. PATENT DOCUMENTS

| | | |
|---|---|---|
| 2007/0228076 A1 | 10/2007 | Horner et al. |
| 2008/0272149 A1 | 11/2008 | Virnelson |
| 2009/0171361 A1 | 7/2009 | Melsheimer et al. |
| 2011/0106054 A1 | 5/2011 | Osborne et al. |

FOREIGN PATENT DOCUMENTS

| | | |
|---|---|---|
| EP | 2269541 A1 | 1/2011 |
| EP | 2446973 A2 | 5/2012 |

* cited by examiner

DISPENSING SYSTEM AND METHOD

CROSS-REFERENCE TO RELATED APPLICATIONS

This application is a divisional application of U.S. patent application Ser. No. 15/612,010, filed on Jun. 2, 2017, which is hereby incorporated by reference herein, in its entirety.

TECHNICAL FIELD

The present disclosure generally relates to medical devices for bone repair, and more particularly to a medical system and method for mixing and dispensing bone cement or other materials.

BACKGROUND

Many medical procedures employ medical grade cement in connection with the restoration and strengthening of bone structures. During such procedures, cement is typically dispensed to a bone to fill in voids or spaces in the bone or between medical devices or implants attached to or embedded within the bone. These dispensing devices may include systems as simple as syringes and as complex as electronically controlled valves.

Due to the medical nature of some procedures, the amount and placement of the fluids, such as, cement, need to be supervised carefully. Despite the simplicity or complexity of the dispensing system, control over when, where and how much cement is dispensed is of concern. Currently, there is a need for an easier bone cement mixer and dispensing tool that would permit for fewer steps or less complicated steps in a mixing and dispensing process. This disclosure describes improvements over these prior art technologies in providing improved systems for dispensing fluids.

SUMMARY

In one embodiment, a dispensing system is provided. The dispensing system includes a device having a body extending along a longitudinal axis between opposite proximal and distal ends. The body includes a proximal chamber, a distal chamber and a wall between the chambers. The body includes a first port in communication with the proximal chamber and a second port in communication with the distal chamber. A shaft is movably positioned within the body. The shaft extending through the wall and comprising a proximal plunger positioned within the proximal chamber and a distal plunger positioned within the distal chamber. Pressure introduced through an opening in the proximal end moves the shaft such that the proximal plunger moves a material within the proximal chamber out of the first port and the distal plunger moves a material within the distal chamber out of the second port. In some embodiments, systems, kits and methods are disclosed.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of a delivery or dispensing system and related methods are discussed in terms of medical devices for the treatment of skeletal injuries, disorders and repairs and more particularly, in terms of a mixing and dispensing system and method for bone repair. In some embodiments, the system and method may be employed in applications such as correction of cracks, fissures, voids, e.g., due to osteoporosis or other diseases or injuries. In addition, the system and method may be employed with the placement of support structures or devices attached to or embedded within bone. For example, such structures may include pins, screws, replacement joints (e.g., of the hip, knee, shoulder), etc.

In some embodiments, the dispensing system includes a device or dispenser, such as, for example, a master cylinder including two materials, such as, for example, separate parts of a two-part epoxy or cement disposed in separate chambers. That is, each part of the cement is included in a different chamber. In some embodiments, the device includes chambers disposed in series so as to synchronize dispensing. In some embodiments, the chambers are coaxial with one another. In some embodiments, the series configuration facilitates control of the mixture ratio. In some embodiments, the device is configured to facilitate use with high pressure applications where space is not readily available. In some embodiments, the device is configured to provide for remote delivery (i.e. out of fluoro range of radiation) and high pressure delivery. In some embodiments, the device provides a minimal footprint and a less cumbersome configuration. In some embodiments, the device maximizes the use of hydraulic pressures by utilizing a dual circuit hydraulic cylinder dispensing system. In some embodiments, the device utilizes hydraulic pressure to simultaneously apply pressure on two plungers or pistons that are mechanically connected in series. In some embodiments, as the pressure is applied to a proximal plunger, force is applied to a distal plunger.

In some embodiments, the device allows for a single hydraulic force to act on two plungers, maximizing output force while minimizing input force. In some embodiments, the device allows for a single hydraulic signal to dispense cement at a 1:1 ratio (or any other ratio) which is critical to ensure proper mixing of materials.

In some embodiments, the master cylinder includes a hydraulic port. In some embodiments, the mixer includes a first and a second chamber. In some embodiments, the device is configured for connection with a CDS cartridge and/or an inflation syringe. In some embodiments, the first chamber includes a plunger and the second chamber includes a plunger. In some embodiments, the first chamber includes a smaller volume due to disposal of a plunger shaft therein. In some embodiments, the second chamber includes a smaller diameter to account for volume differential. In some embodiments, the first chamber includes a first material. In some embodiments, the second chamber includes a second material. In some embodiments, the first chamber is configured with a port to expel the first material to a static mixer. In some embodiments, the second chamber includes a port to expel the second material to the static mixer.

In some embodiments, the device includes a rod or shaft disposed with the first chamber configured with a diameter equal to the CDS cartridge. In some embodiments, the first chamber includes a seal configured to resist and/or prevent material from mixing within the chamber. In some embodiments, the second chamber includes an air vent. In some embodiments, the ports are configured for connection with tubing such as, for example, ¾ inch tubing. In some embodiments, the ports include universal end caps for connection with the tubing. In some embodiments, the plunger in the first chamber includes a slot for engagement with an instrument such as, for example, a driver.

In some embodiments, the device expels the materials through the ports to a static mixer. In some embodiments, the static mixer includes a mixing blade. In some embodiments, the ports a disposed perpendicular to an axis of the mixer. In some embodiments, the ports are disposed transverse to an axis of the mixer. In some embodiments, the static mixer is connected with a cannula so that the materials mixed within the static mixer can move through the cannula for delivery to a surgical site. In some embodiments, the device is configured for connection with a dual chamber plunger. In some embodiments, the dual chamber plunger is connected with the static mixer.

In some embodiments, one or all of the components of the dispensing system may be disposable, peel-pack, pre-packed sterile devices. One or all of the components of the dispensing system may be reusable. The dispensing system may be configured as a kit with multiple sized and configured components. In some embodiments, one or more of the components of the dispensing system are configured to be sterilized.

In some embodiments, the present disclosure may be employed to treat or repair bone injuries or disorders such as, for example, osteoporosis, joint replacement, fracture repairs, bone breaks, etc. It is contemplated that the present disclosure may be employed with other osteal and bone related applications, including those associated with diagnostics and therapeutics, such as the delivery of a therapeutic agents to a site for treatment or the delivery of radio opaque markers for tracking fluid once it is released into a patient. In some embodiments, the disclosed dispensing system and methods may be alternatively employed in a surgical treatment with a patient in a prone or supine position, and/or employ various surgical approaches, including anterior, posterior, posterior mid-line, direct lateral, postero-lateral, antero-lateral approaches, etc. in any body region. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a dispensing system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-14, there are illustrated components of a delivery system, such as, for example, a dispensing system 10 in accordance with the principles of the present disclosure.

The components of system 10 can be fabricated from biologically acceptable materials suitable for medical applications, including metals, synthetic polymers, ceramics and bone material and/or their composites, depending on the particular application and/or preference of a medical practitioner. For example, the components of system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 is employed, for example, with an open, mini-open or minimally invasive surgical technique to fill voids, provide patches, attach prosthetic devices, etc., or any other bone related repairs. In some embodiments, system 10 is used to mix and/or deliver a material, such as, for example, a cement. In some embodiments, the cement is a two-part cement wherein the parts are mixed immediately before the cement is delivered to a location, such as, for example, a surgical site. In some embodiment, the surgical site is bone, such as, for example, a bone defect, fracture or void. In some embodiments, the components of the cement are viscous and thus require a high amount of pressure to move the components of the cement through a device or devices, such as, for example, the components of system 10.

System 10 includes a device, such as, for example, a master cylinder or dispenser 12. Dispenser 12 includes a body 14 that extends along a longitudinal axis L between an end 16 and an opposite end 18. End 16 includes a chamber 20 and end 18 includes a chamber 22. Chamber 20 is coaxial with chamber 22 and longitudinal axis L. Body 14 comprises a wall 24 between chambers 20, 22. Body 14 further comprises a port 26 that is in communication with chamber 20 and a port 28 that is in communication with chamber 22. Port 26 is spaced apart from port 28. In some embodiments, chambers 20, 22 each have the same length. In some embodiments, chamber 20 has a length that is less than or greater than the length of chamber 22. In some embodiments, chamber 20 and/or chamber 22 has a uniform width or diameter. In some embodiments, chamber 20 and/or chamber 22 may have various cross section configurations, such as, for example, circular, oval, oblong, triangular, rectangular, square, polygonal, irregular, uniform, non-uniform, variable, tubular and/or tapered. In some embodiments, port 26 and/or port 28 may be disposed at alternate orientations, relative longitudinal axis L, such as, for example, parallel, transverse, perpendicular and/or other angular orientations such as acute or obtuse, co-axial and/or may be offset or staggered. In some embodiments, body 14 includes one or more pressure relief valves that is in communication with chamber 20 and/or chamber 22 to release pressure within chamber 20 and/or chamber 22.

In some embodiments, dispenser 12 includes a cap 30 coupled to end 16 and a cap 32 coupled to end 18. Cap 30 is configured to be coupled to delivery device and cap 32 is configured to be coupled to a mixing device, as discussed herein. Cap 30 includes an opening 34 that is in communication with chamber 20 and cap 32 includes an opening 36 that is communication with chamber 22. In some embodiments, opening 36 defines at least a portion of port 28. In some embodiments, opening 34 and/or opening 36 may be disposed at alternate orientations, relative to longitudinal axis L, such as, for example, parallel, transverse, perpendicular and/or other angular orientations such as acute or obtuse, co-axial and/or may be offset or staggered. In some embodiments, opening 34 and/or opening 36 may have various cross section configurations, such as, for example, circular, oval, oblong, triangular, rectangular, square, polygonal, irregular, uniform, non-uniform, variable, tubular and/or tapered. In some embodiments, the diameters of one or more of chambers 20, 22 and/or ports 26, 28 can be adjusted to vary the amount of pressure created when materials move through chambers 20, 22 and/or ports 26, 28. That is, one or more of chambers 20, 22 and/or ports 26, 28 can include a smaller diameter when a high amount of pressure is needed to move materials through chambers 20, 22 and/or ports 26, 28. Alternatively, one or more of chambers 20, 22 and/or ports 26, 28 can include a larger diameter when a high amount of pressure is needed to move materials through chambers 20, 22 and/or ports 26, 28.

In some embodiments, end 16 has a threaded outer surface that is configured to engage a threaded inner surface of cap 30. In some embodiments, end 18 has a threaded outer surface that is configured to engage a threaded inner surface of cap 32. In some embodiments, the threaded inner surface of cap 30 defines a portion of a cavity 38. The threaded outer surface of end 16 and an inner surface of end 16 that defines chamber 20 is positioned within cavity 38 to couple cap 30 to body 14. In some embodiments, the threaded inner surface of cap 32 defines a portion of a cavity 40. The threaded outer surface of end 18 and an inner surface of end 18 that defines chamber 22 is positioned within cavity 40 to couple cap 32 to body 14. In some embodiments, cap 30 and/or cap 32 can be variously connected with body 14, such as, for example, monolithic, integral connection, frictional engagement, threaded engagement, mutual grooves, screws, adhesive, nails, barbs and/or raised element.

Dispenser 12 comprises a rod, such as, for example, a shaft 42 having a plunger 44 and a plunger 46 that is spaced apart from plunger 44 by shaft 42. In some embodiments, shaft 42 is coaxial with longitudinal axis L. Plungers 44, 46 are disposed on opposite ends of shaft 42. In some embodiments, plunger 44 defines a proximal end surface of shaft 42 and plunger 46 defines a distal end surface of shaft 42. Shaft 42 is movably disposed within body 14 so that shaft 42 can translate relative to body 14 in opposite directions along longitudinal axis L. Shaft 42 extends through a passageway 45 in wall 24 such that plunger 44 is positioned within chamber 20 and plunger 46 is positioned within chamber 22. In some embodiments, at least one of plunger 44 and/or plunger 46 is permanently fixed to shaft 42. In some embodiments, at least one of plunger 44 and/or plunger 46 is removably attached to shaft 42. In some embodiments, plunger 44 includes a groove having a seal, such as, for example, an o-ring 48 disposed therein. O-ring 48 engages an inner surface of body 14 that defines chamber 20 to form a water and/or airtight seal. In some embodiments, plunger 46 includes a groove having a seal, such as, for example, o-ring 48 disposed therein. O-ring 48 engages an inner surface of body 14 that defines chamber 22 to form a water and/or airtight seal. In some embodiments, o-ring 48 comprises rubber and/or another elastomeric material, such as, for example, silicone.

Figure 1:
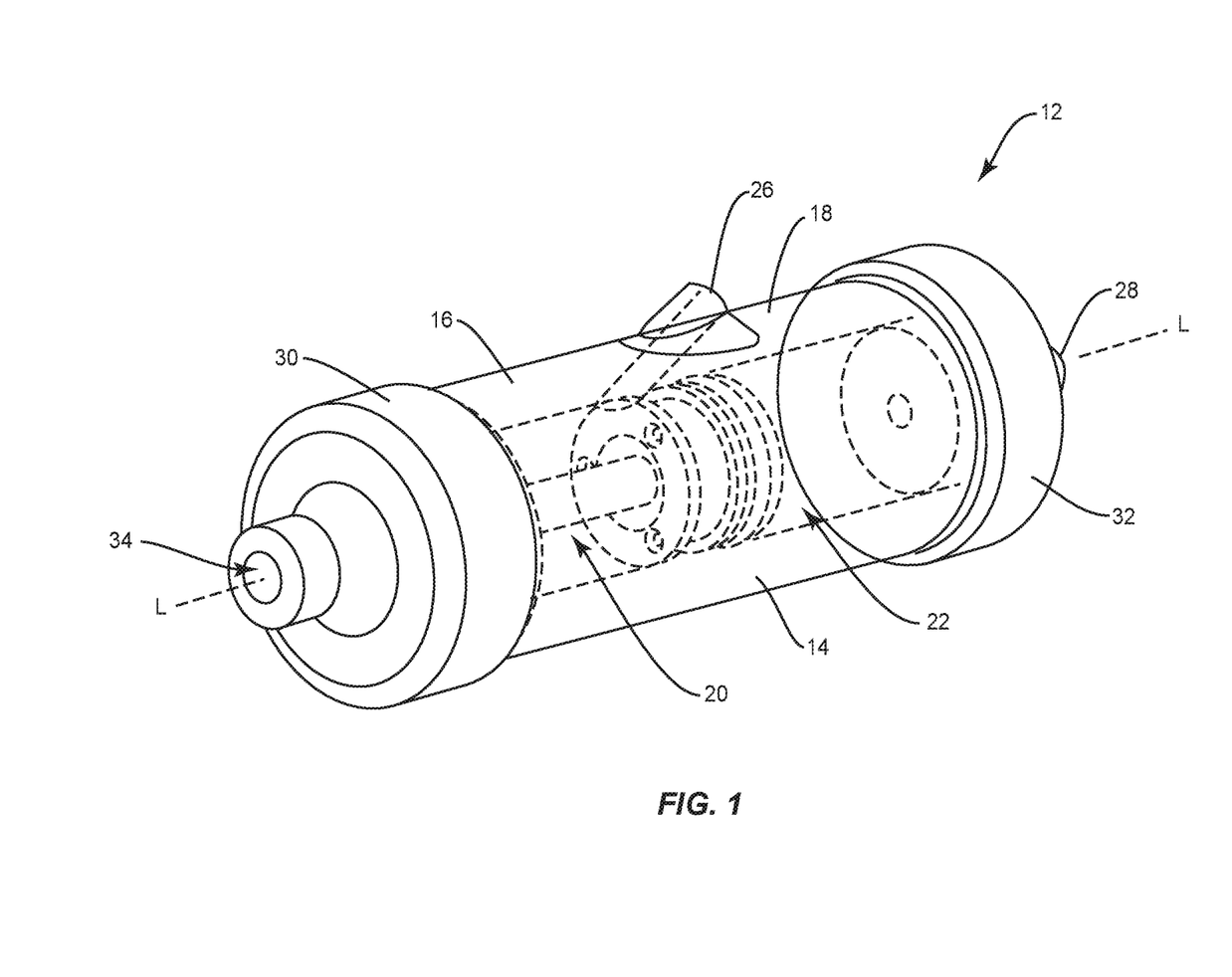
FIG. 1 is a perspective view, in part phantom, of one embodiment of components of a dispensing system in accordance with the present principles.
Figure 2:
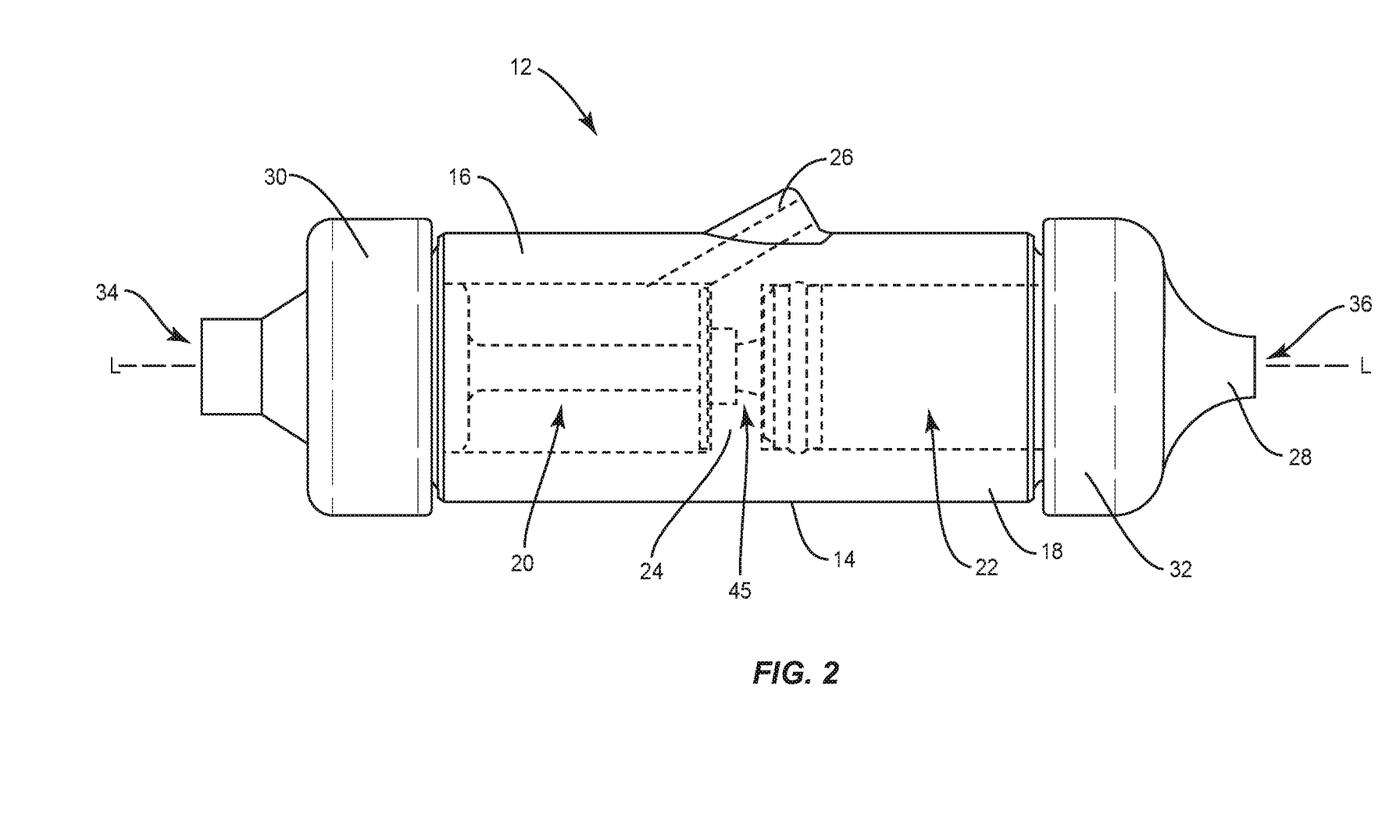
FIG. 2 is a side view, in part phantom, of the components shown in FIG. 1.
Figure 3:
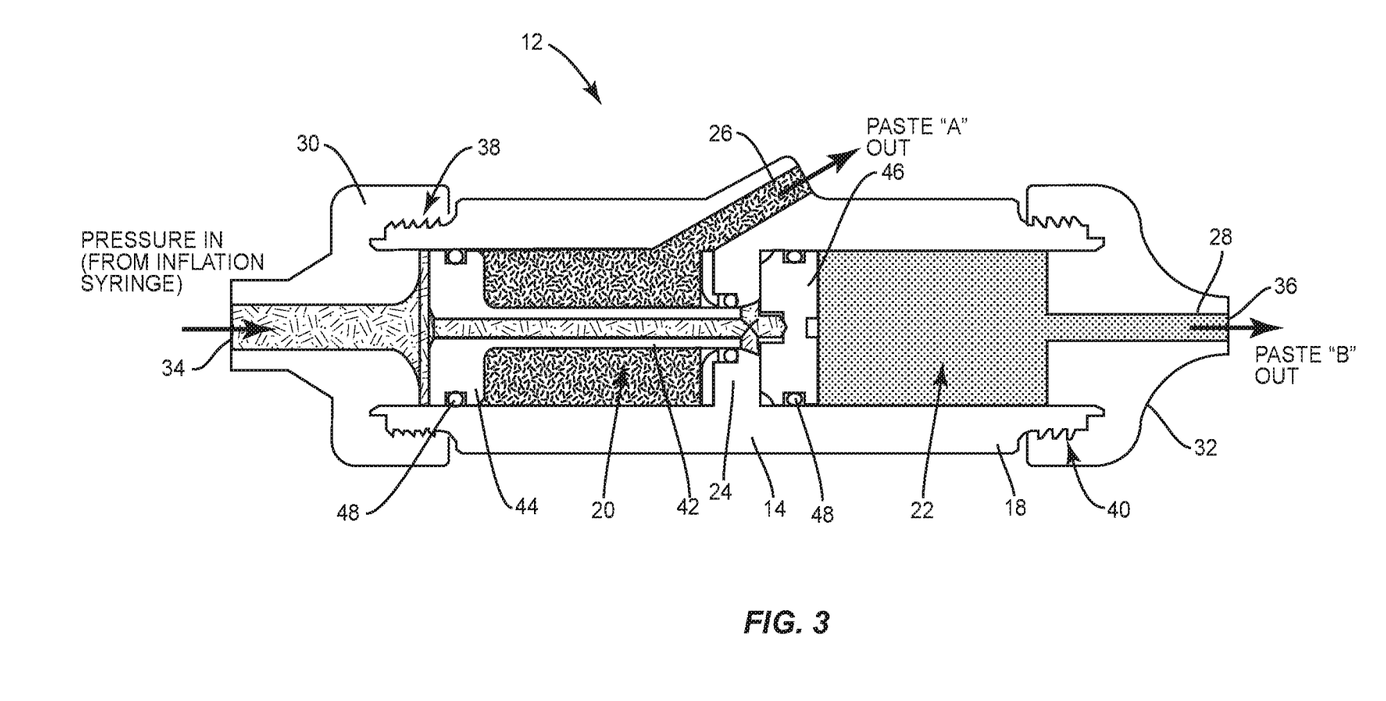
FIG. 3 is a side, cross-sectional view of the components shown in FIG. 1.
Figure 4:
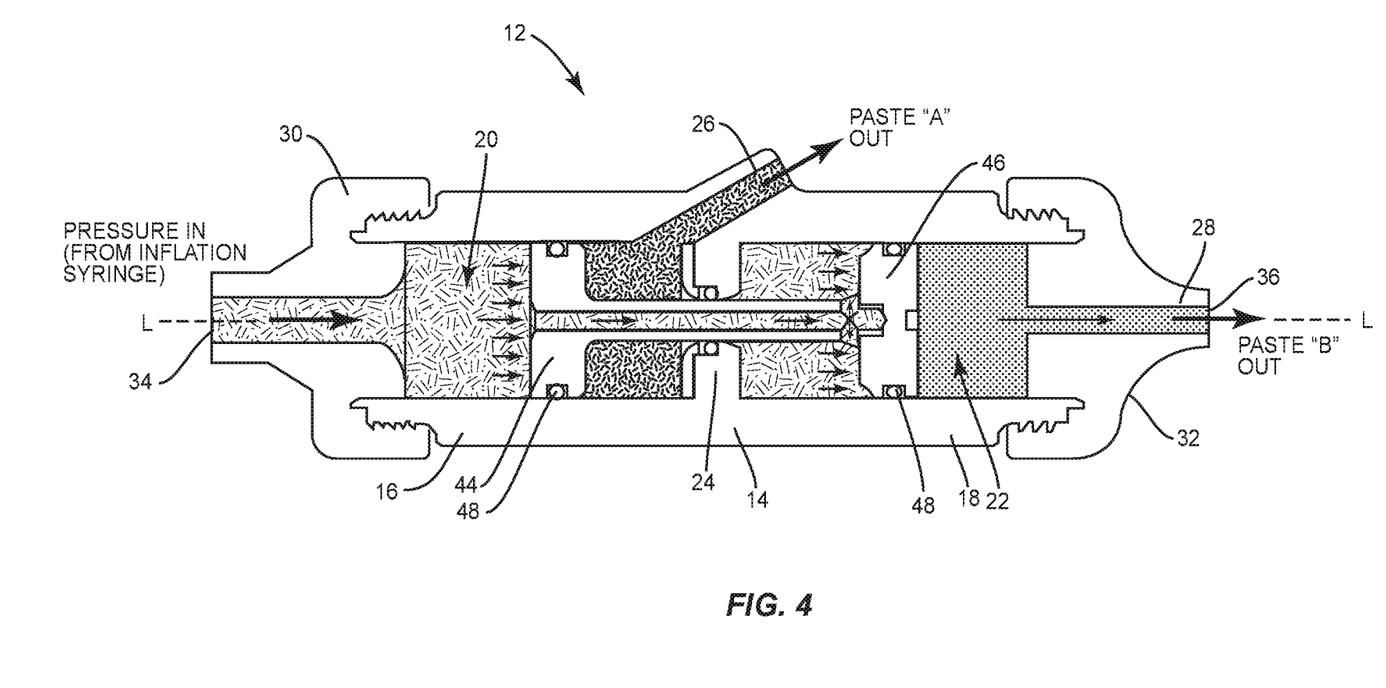
FIG. 4 is a side, cross-sectional view of the components shown in FIG. 1.
Figure 5:
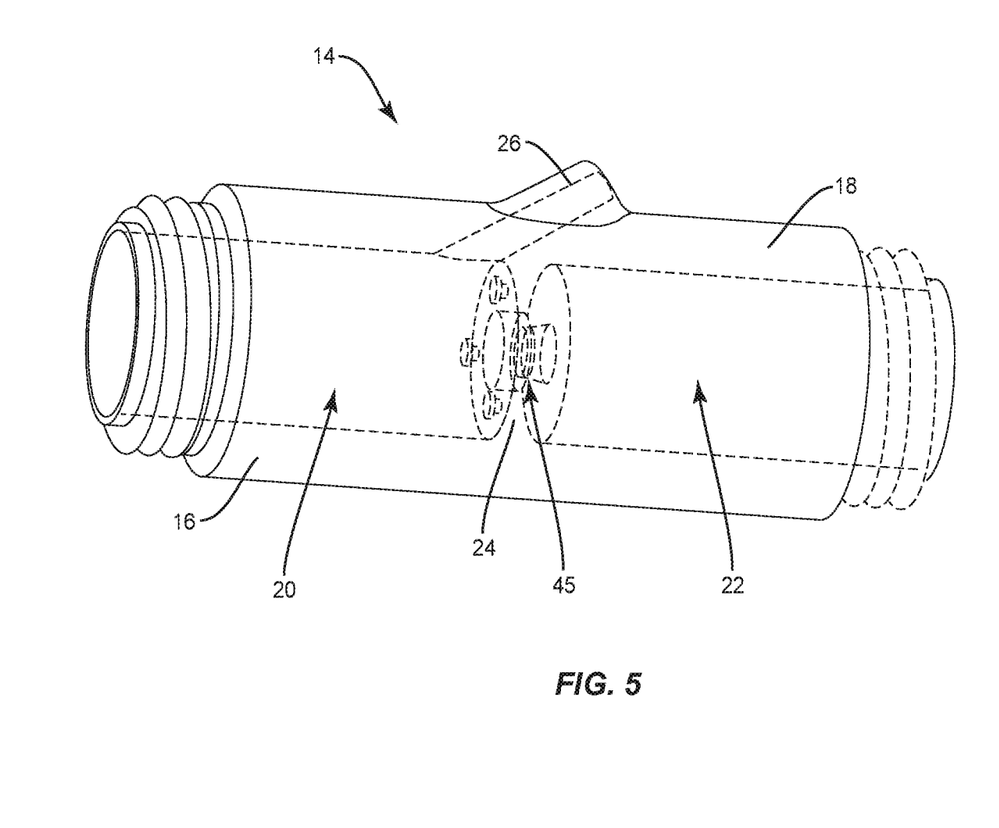
FIG. 5 is a perspective view, in part phantom, of one of the components shown in FIG. 1.
Figure 6:
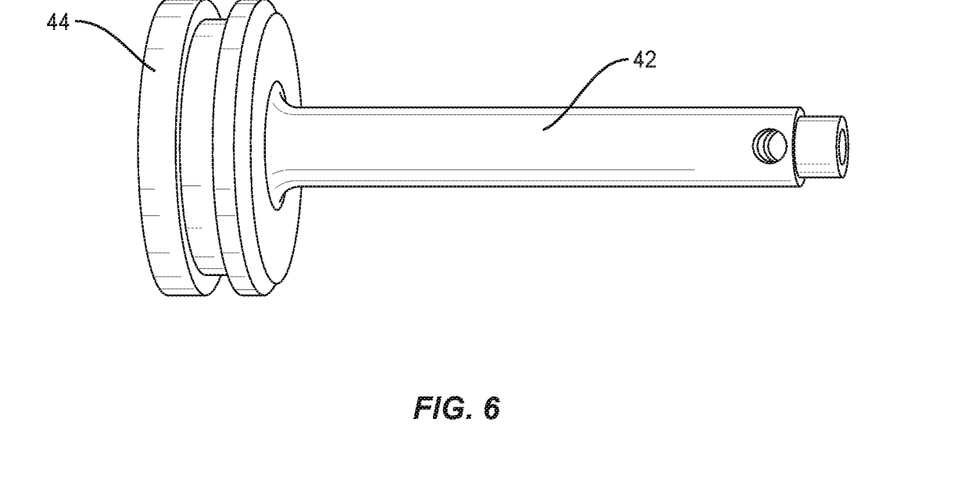
FIG. 6 is a perspective view of a portion of one of the components shown in FIG. 1.
Figure 7:
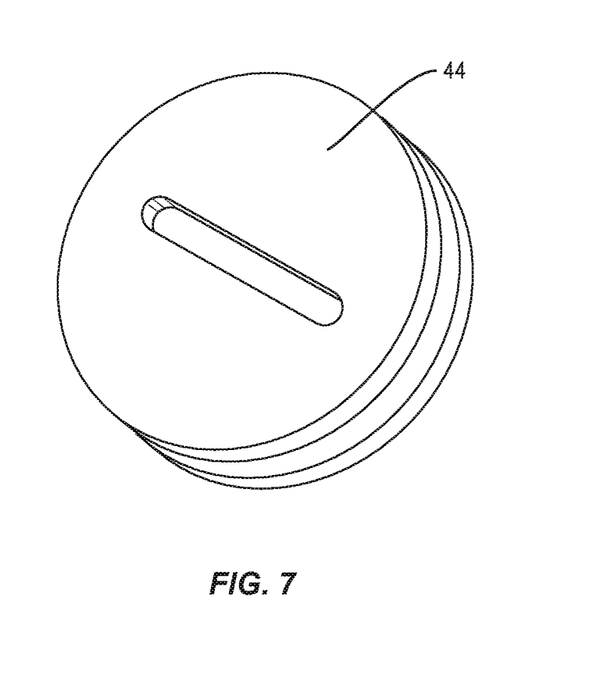
FIG. 7 is a perspective view of a portion of one of the components shown in FIG. 1.
Figure 8:
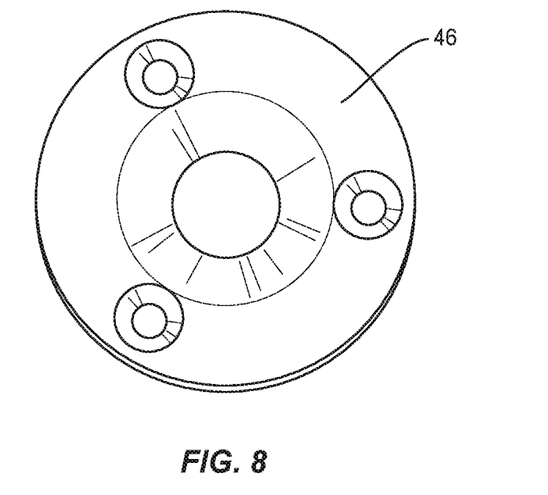
FIG. 8 is an end view of a portion of one of the components shown in FIG. 1.
Figure 9:
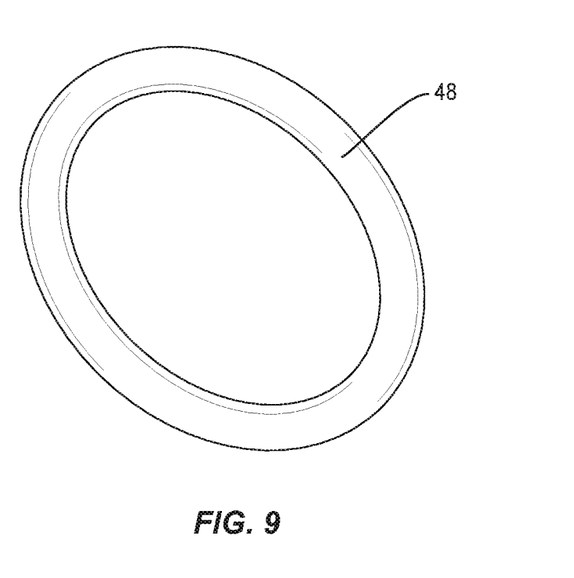
FIG. 9 is a perspective view of a portion of one of the components shown in FIG. 1.
Figure 10:
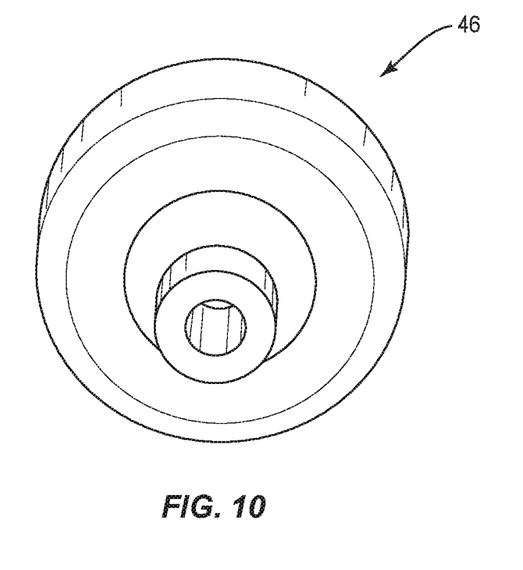
FIG. 10 is a perspective view of a portion of one of the components shown in FIG. 1.
Figure 11:
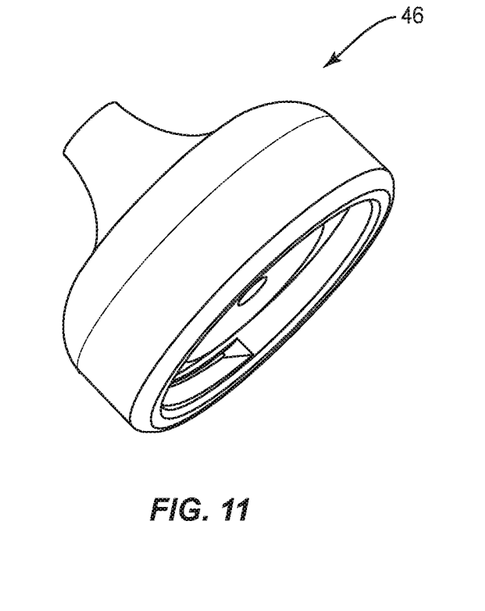
FIG. 11 is a perspective view of a portion of one of the components shown in FIG. 1.
Figure 12:
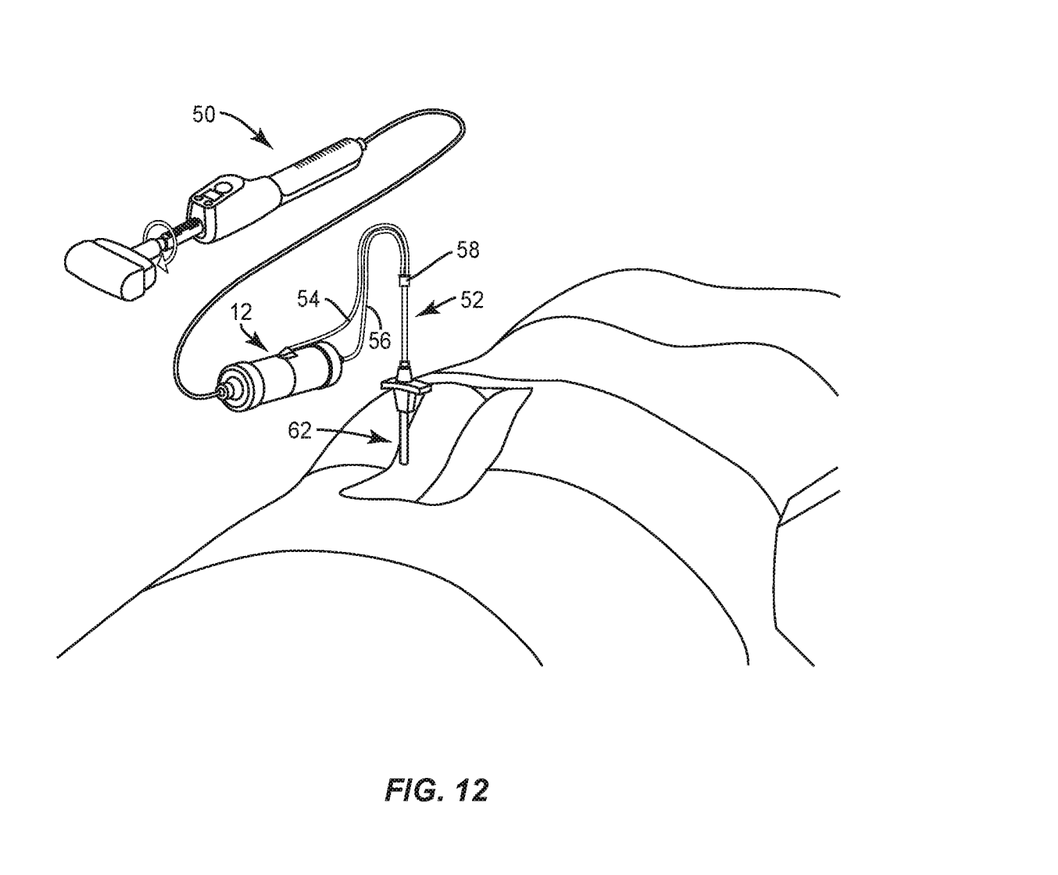
FIG. 12 is a perspective view of components of the dispensing system.

A delivery device, such as, for example, an inflation syringe 50 is coupled to cap 30 to deliver pressure, such as, for example, hydraulic pressure through opening 34 such that the pressure moves shaft 42 along longitudinal axis L in the direction shown by arrow A in FIG. 3. In some embodiments, the pressure is created by a gas or fluid that is moved from syringe 50 and into dispenser 12. In some embodiments, the gas or fluid is air, water, hydraulic fluid, etc. As shaft 42 moves along longitudinal axis L in the direction shown by arrow A, plungers 44, 46 also move along longitudinal axis L in the direction shown by arrow A. As plungers 44, 46 move along longitudinal axis L in the direction shown by arrow A, plunger 44 moves a material, such as, for example, a paste in chamber 20 out of chamber 20 through port 28 and plunger 46 moves a material, such as, for example, a paste in chamber 22 out of chamber 22 through port 30. In some embodiments, plunger 44, 46 move the materials out of ports 26, 28 simultaneously. In some embodiments, the materials move out of ports in a 1:1 ratio. In some embodiments, the materials are components of a cement, such as, for example, a two-part cement. In some embodiments, the cement polymerizes quickly once the components of the cement are mixed. As such, the components of the cement must be separated and mixed immediately prior to applying the cement to a location, such as, for example, bone. In some embodiments, the configuration of dispenser 12 requires a pressure of about 700 psi to move the materials through chambers 20, 22 and/or ports 26, 28. That is, the configuration of dispenser 12 allows the materials to be moved through chambers 20, 22 and/or ports 26, 28 even when the materials are relatively viscous. In other devices, that include parallel chambers that are not coaxial with one another (in series), higher amounts of pressure are required to move materials through the device. This allows system 10 to include a delivery device that is not required to create higher pressures, thus reducing the cost of system 10.

Figure 13:
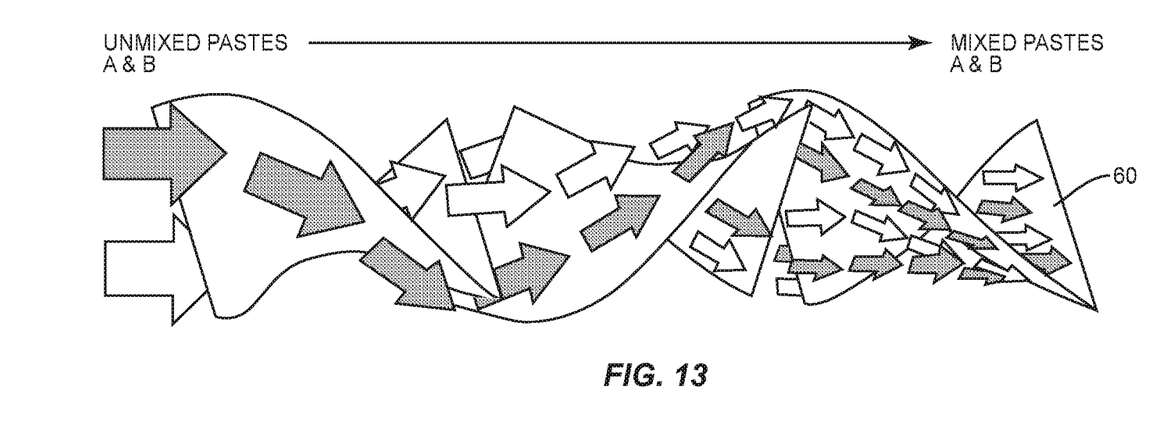
FIG. 13 is a side view of a portion of one of the components shown in FIG. 12.
Figure 14:
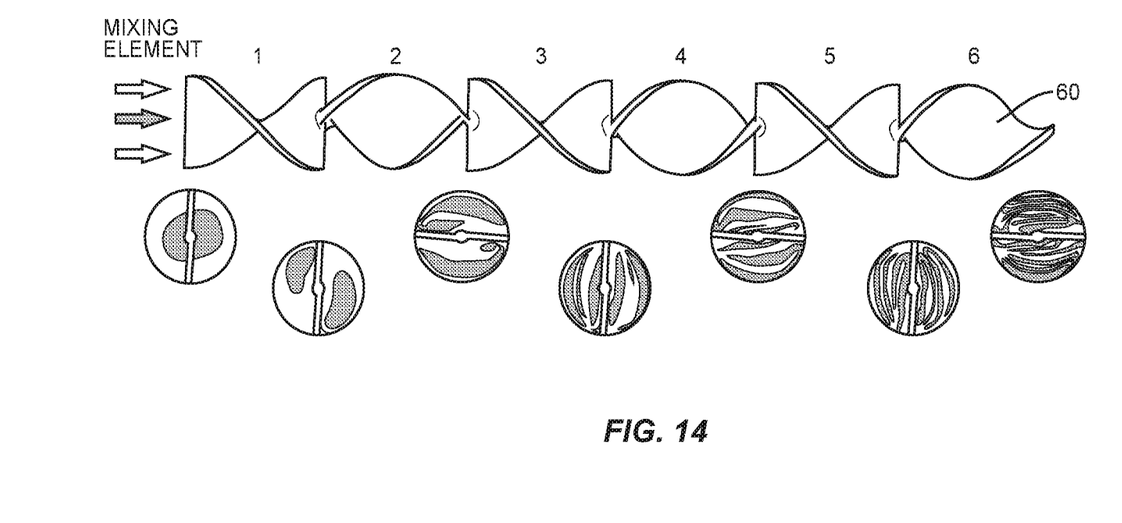
FIG. 14 is a side view of a portion of one of the components shown in FIG. 12.

Dispenser 12 is coupled to a mixing device, such as, for example, a static mixer 52. In some embodiments, dispenser 12 is connected to mixer 52 by hollow tubes, such as for example a tube 54 that is coupled to port 26 and a tube 56 that is coupled to port 28. First ends of tubes 54, 56 are coupled ports 26, 28 and second ends of tubes 54, 56 are coupled to a connector 58 of mixer 52. Mixer 52 includes a mixing element, such as, for example, a helical blade 60 positioned within a body of mixer 52. In some embodiments, blade 60 is fixed relative to the body of mixer 52. In some embodiments, blade 60 is rotatable relative to the body of mixer 52. The pressure from syringe 50 moves the materials through tubes 54, 56 and into the body of mixer 52 after the materials exit ports 26 28. The materials exit tubes 54, 56 and move into the body of mixer 52. As the materials move through the body of mixer 52, blade 60 mixes the materials, as shown in FIG. 13, for example. In some embodiments, blade 60 remains fixed relative to the body of mixer 52 as the materials move through mixer 52. In some embodiments, blade 60 rotates relative to the body of mixer 52 as the materials move through mixer 52 to facilitate mixing of the materials. In some embodiments, mixing the materials creates a cement that begins to polymerize when the materials are combined and/or mixed. In some embodiments, mixing the materials creates a cement that begins to polymerize shortly (within a seconds or minutes) after the materials are combined and/or mixed. In some embodiments, tubes 54, 56 each have a length sufficient to distance syringe 50 out of a field of radiation.

In some embodiments, mixer 52 is coupled to a cannula, such as, for example, a cannula 62. The mixed materials exit mixer 52 through a distal opening in mixer 52 and move through cannula 62. The mixed material exit cannula 62 through a distal opening in cannula to deliver the mixed material to a location, such as, for example, a surgical site.

In assembly, operation and use, system 10 is employed with a surgical procedure, such as, for a treatment of bone injuries, to provide bone repairs, to strengthen or rebuild bones, etc. It is contemplated that one or all of the components of system 10 can be delivered or implanted as a pre-assembled device or can be assembled in situ. System 10 may be completely or partially revised, removed or replaced.

For example, system 10 and accessories thereof, described above, can be employed during a surgical procedure for mixing and dispensing a cement, such as, for example, bone cement. In use, a medical practitioner obtains access to a surgical site including a bone in any appropriate manner, such as through incision and retraction of tissues. It is envisioned that system 10 can be used in any existing surgical method or technique including open surgery, mini-open surgery, minimally invasive surgery and percutaneous surgical implantation, whereby the bone is accessed through a mini-incision, or sleeve that provides a protected passageway to the area. Once access to the surgical site is obtained, the particular surgical procedure can be performed for treating or repairing the bone.

An incision is made in the body of a patient and a cutting instrument (not shown) creates a surgical pathway for implantation of components of system 10. A preparation instrument (not shown) can be employed to prepare tissue surfaces of the bone, as well as for aspiration and irrigation of a surgical region according to the requirements of a particular surgical application.

Holes, fractures, voids, depressions, etc. may exist in the bone or may be created in the bone as part of the procedure. After appropriate steps are taken for the treatment or repair, these holes, fractures, voids, depressions, etc. are filled with the mixed bone cement to maintain or improve the bone's structural integrity. Components of system 10 are delivered to the surgical site along the surgical pathway(s) and into or onto bone tissue.

In one embodiment, system 10 may also deliver an agent, which may be mixed in the bone cement or delivered separately. That is, the agent may be included in the material that is pre-loaded into chamber 20 and/or the material that is pre-loaded into chamber 22. In some embodiments, the material that is pre-loaded into chamber 20 may include a first agent and the material that is pre-loaded into chamber 22 may include a second agent that is different than the first agent.

In some embodiments, the agent(s) may include bone growth promoting material. In some embodiments, the agent(s) may include therapeutic polynucleotides or polypeptides. It is further contemplated that the agent(s) may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. In some embodiments, the agent(s) may include one or a plurality of therapeutic agents and/or pharmacological agents for release, including sustained release, to treat, for example, pain, inflammation and degeneration.

In some embodiments, the components of correction system 10 can be made of radiolucent materials such as polymers. Radiomarkers may be included for identification under x-ray, fluoroscopy, CT or other imaging techniques.

It is envisioned that the use of microsurgical and image guided technologies may be employed to access, view and repair bone deterioration or damage, with the aid of the system 10. Upon completion of the procedure, the surgical instruments and assemblies are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method of mixing cement, comprising:
   introducing pressure from a delivery device through an opening in a proximal end of a body of a dispenser such that the pressure moves a shaft of the dispenser along a longitudinal axis defined by the dispenser,
   the shaft comprising a proximal plunger positioned in a proximal chamber of the body and a distal plunger positioned in a distal chamber of the body, wherein moving the shaft along the longitudinal axis moves the proximal plunger to push a material within the proximal chamber out of a first port of the body and moves the distal plunger to push a material within the distal chamber out of a second port of the body,
   wherein the pressure moves the materials through the ports and into a mixing device, the materials being mixed within the mixing device to form a cement.

2. A method as recited in claim 1, wherein the pressure moves the cement out of the mixing device to deliver the cement to a location.

3. A method as recited in claim 2, wherein the location is a bone defect.

4. A method as recited in claim 1, wherein a wall is positioned between the proximal chamber and the distal chamber, the shaft extending through the wall.

5. A method as recited in claim 1, wherein the delivery device is a syringe and the pressure introduced by the syringe is hydraulic pressure.

6. A method as recited in claim 1, wherein the materials through the ports in a 1:1 ratio.

7. A method as recited in claim 1, wherein:
   the mixing device is coupled to a cannula; and
   the pressure moves the cement out of the mixing device and through the cannula to deliver the cement to a location.

8. A method as recited in claim 1, wherein the mixing device comprises a helical blade positioned within a body of the mixing device, the materials being mixed by the helical blade as the materials move through the mixing device.

9. A method as recited in claim 8, wherein the helical blade rotates relative to the body of the mixing device as the materials move through the mixing device.

10. A method as recited in claim 8, wherein the helical blade is fixed relative to the body of the mixing device as the materials move through the mixing device.

11. A method as recited in claim 1, wherein the mixing device is coupled to the dispenser by a first tube and a second tube.

12. A method as recited in claim 11, wherein the first tube is coupled to the first port and the second tube is coupled to the second port such that the material in the proximal chamber moves through the first tube to the mixing device and the material in the distal chamber moves through the second tube to the mixing device.

13. A surgical method comprising:
    coupling a delivery device to a dispenser;
    introducing hydraulic pressure from the delivery device through an opening in a proximal end of a body of the dispenser such that the hydraulic pressure translates a shaft of the dispenser relative to the body to push a material within a proximal chamber of the dispenser out of a first port of the body and to push a material within a distal chamber of the dispenser out of a second port of the body; and
    mixing the materials within the mixing device to form a cement.

14. A method as recited in claim 13, wherein a wall is positioned between the proximal chamber and the distal chamber, the shaft extending through the wall.

15. A method as recited in claim 13, wherein the materials move out of the ports simultaneously.

16. A method as recited in claim 13, wherein the materials through the ports in a 1:1 ratio.

17. A method as recited in claim 13, further comprising:
    coupling the dispenser to a mixing device;
    coupling the mixing device to a proximal end of a cannula;
    positioning a distal end of the cannula adjacent to a bone defect; and
    mixing the materials within the mixing device to form a cement,
    wherein the hydraulic pressure moves the cement out of the mixing device and through the cannula to deliver the cement to the bone defect.

18. A method as recited in claim 17, wherein the mixing device comprises a helical blade positioned within a body of the mixing device, the materials being mixed by the helical blade as the materials move through the mixing device, the helical blade being fixed relative to the body of the mixing device as the materials move through the mixing device.

19. A method as recited in claim 13, wherein the mixing device is coupled to the dispenser by a first tube and a second tube, the first tube being coupled to the first port and the second tube being coupled to the second port such that the material in the proximal chamber moves through the first tube and into the mixing device and the material in the distal chamber moves through the second tube and into the mixing device.

20. A surgical method comprising:
- positioning a distal end of a cannula adjacent to a bone fracture;
- coupling a proximal end of a static mixing device to a proximal end of the cannula, the mixing device comprising a helical blade fixed within a body of the mixing device;
- coupling a dispenser to the mixing device, the dispenser comprising a body extending along a longitudinal axis between opposite proximal and distal ends, the body comprising a proximal chamber, a distal chamber and a wall between the chambers, the body including a first port in communication with the proximal chamber and a second port in communication with the distal chamber, the dispenser comprising a shaft movably positioned within the body, the shaft extending through the wall and comprising a proximal plunger positioned within the proximal chamber and a distal plunger positioned within the distal chamber;
- coupling a syringe to the dispenser;
- introducing hydraulic pressure from the syringe through an opening in the proximal end of the body such that the hydraulic pressure translates the shaft relative to the body to push a material within the proximal chamber out of the first port and into the mixing device and to push a material within the distal chamber out of the second port and into the mixing device; and
- mixing the materials within the mixing device to form a cement,
- wherein the hydraulic pressure moves the cement out of the mixing device and through the cannula for delivery to the bone fracture.

\* \* \* \* \*